United States Patent [19]

Herrick

[11] Patent Number: 4,575,877
[45] Date of Patent: Mar. 18, 1986

[54] INTRAOCULAR LENS HAVING LOOPS DEFINING A POSTERIOR CAPSULE BARRIER

[76] Inventor: Robert S. Herrick, 1255 Via Del Rey, South Pasadena, Calif. 91030

[21] Appl. No.: 520,455

[22] Filed: Aug. 4, 1983

[51] Int. Cl.⁴ .......................... A61F 1/16; A61F 1/24
[52] U.S. Cl. ................................................ 623/6
[58] Field of Search ......................................... 3/13, 1

[56] References Cited

U.S. PATENT DOCUMENTS

| | | | |
|---|---|---|---|
| 4,159,546 | 7/1979 | Shearing | 3/13 |
| 4,244,060 | 1/1981 | Hoffer | 3/13 |
| 4,412,359 | 11/1983 | Myers | 3/13 |
| 4,485,499 | 12/1984 | Castleman | 3/13 |

OTHER PUBLICATIONS

Pallin, M. D., Samuel L. and Walman, M. D., Gerald B., "Posterior Chamber Intraocular Lens Implant Centration: In or Out of 'the Bag,'" *AM Intra-Ocular Implant Society Journal*, vol. 8, Summer 1982, pp. 254-257.
Hoffer, M. D., F.A.C.S., Kenneth J., "The Hoffer Ridge Lenses from Cilco" (product brochure, 7 pages), Mar. 1983.
"IOLAB Model 103 (J/M/L) Sinskey Posterior Chamber Lens," IOLAB Corporation product brochure (4 pages).
"Laser Damages Compared in Glass & PMMA Lenses," *IOL & Ocular Surgery News*, Jun. 15, 1983, pp. 4-5.
"Cilco's Nd: YAG-An Ophthalmic Laser System Designed for the Future" (product brochure), Mar. 1983.

*Primary Examiner*—Ronald L. Frinks
*Attorney, Agent, or Firm*—Daniel J. Meaney, Jr.

[57] ABSTRACT

An intraocular lens having a lens body which is adapted to pass through the iris of an eye and a pair of pliable loops, each having a generally planar mounting end located at one end thereof and which terminates at the opposite end thereof in a supporting end extending at a selected acute angle from the mounting end wherein the mounting end is formed into a generally arcuate shape which terminates in a protuberant member having a predetermined length which extends substantially normal from the plane of said mounting end in a direction of the angle defined by the supporting end and wherein the supporting end has the distal end thereof formed into an arcuate-shaped loop located in a plane which extends substantially at the selected angle and wherein the pair of pliable loops have the protuberant members affixed posteriorly to the lens body at selected locations wherein the arcuate-shaped mounting ends define a posterior capsule barrier which is adapted to be positioned contiguous to a posterior capsule of an eye while being capable of defining a space between the lens and the posterior capsule of the eye.

17 Claims, 14 Drawing Figures

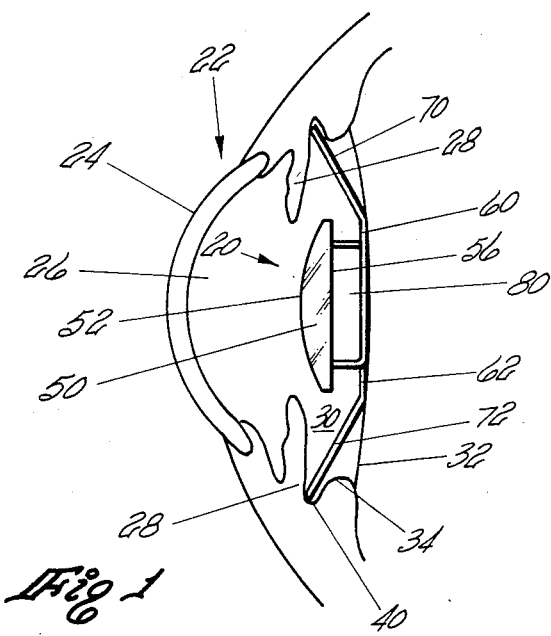
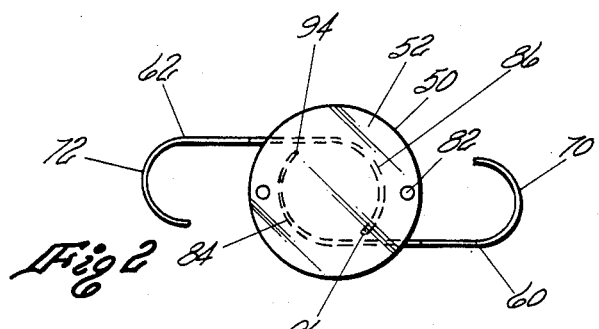
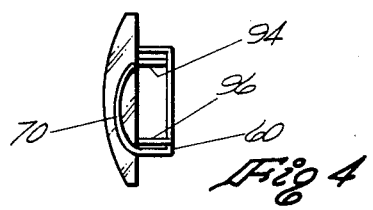
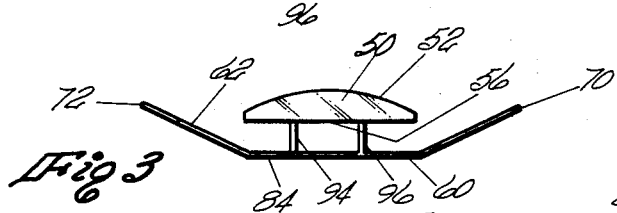
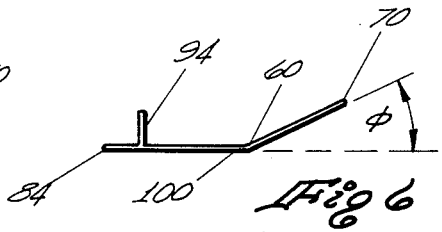
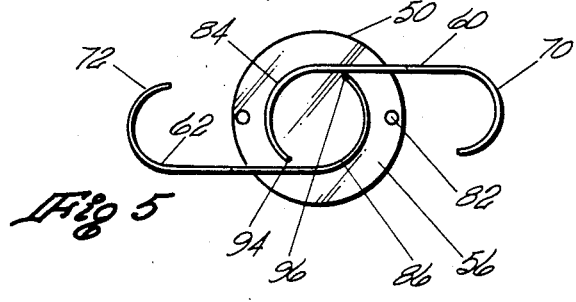
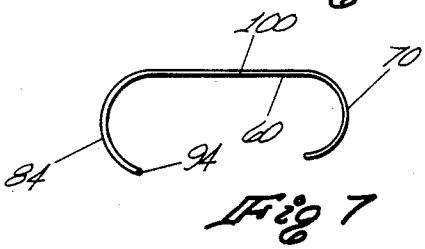

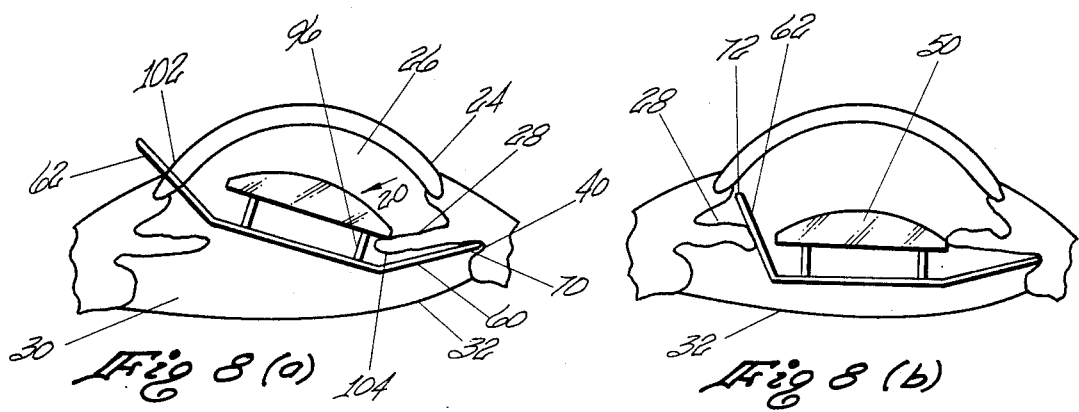
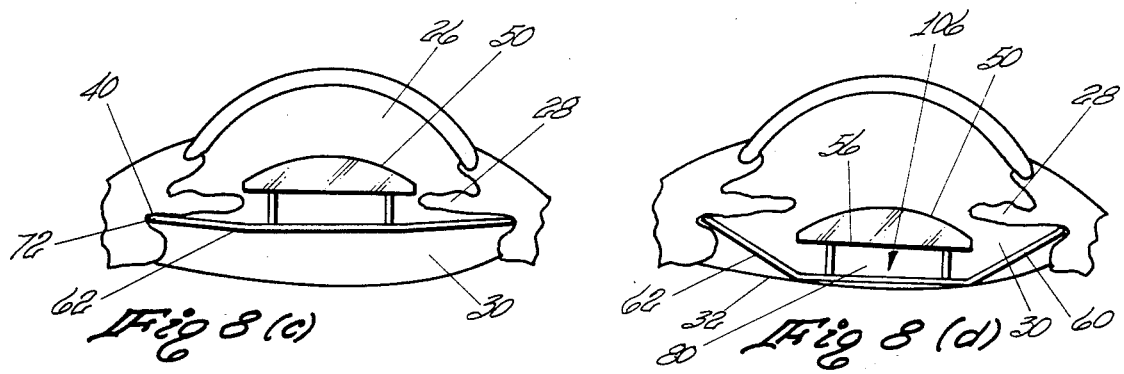
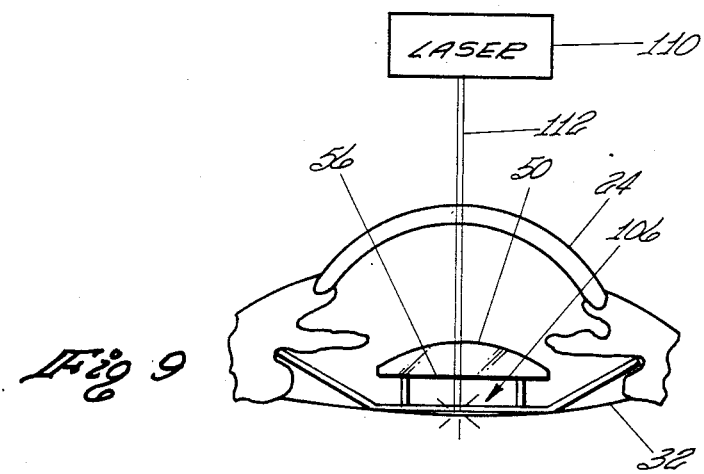
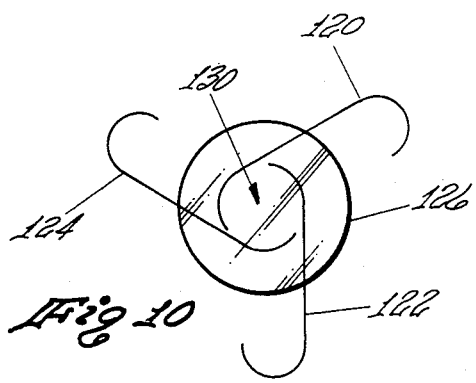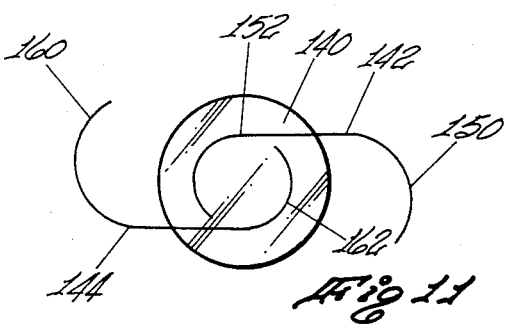

INTRAOCULAR LENS HAVING LOOPS DEFINING A POSTERIOR CAPSULE BARRIER

BACKGROUND OF THE INVENTION

1. Field of the Invention

This invention relates to an intraocular lens adapted for implantation in the posterior chamber of an eye after intracapsular or extracapsular cataract extraction and more particularly to an intraocular lens having loops extending posteriorly rearward of the lens which are adapted to center the lens within the posterior chamber and wherein the loops engage the posterior capsule while maintaining a spaced relationship between the rear of the lens and the posterior capsule.

2. Description of the Prior Art

In the human eye, a cataract condition results when the tissue within the lens capsule of the eye becomes clouded and obstructs the passage of light. There are two known methods or forms of surgery used to correct this condition; namely, an intracapsular cataract extraction and an extracapsular cataract extraction. In an intracapsular cataract extraction, the entire lens of the eye is removed intact. In such surgery, the zonules or suspensory ligaments about the entire periphery of the capsule, including the posterior capsule, are removed intact such that the occluded material is likewise removed intact. In an extracapsular cataract extraction, the surgeon makes an incision through the annular capsule of the lens and removes the occluded material from the capsule through the incision. In performing the extracapsular cataract extraction, the surgeon may find it necessary to utilize suction, scraping or other techniques to fully extract the clouded cellular material. However, the transparent rear capsule wall of the eye, or the posterior capsule, remains in place in the eye. Also remaining in place are the zonules and the peripheral portions of the anterior capsule, which are generally referred to as the interior capsule flaps.

It is becoming increasingly important for medical and other reasons to perform extracapsular cataract extractions, which are more difficult to perform than an intracapsular cataract extraction. The reasons for extracapsular cataract extractions becoming more desirable is that the posterior capsule remains in place which, in turn, causes the vitreous fluid located behind the posterior capsule to remain in place. If the posterior capsule is removed at the time of surgery, the vitreous fluid, which is a jelly-like material, may rupture through the posterior chamber and into the pupil of the eye, which may result in adverse, undesirable side effects. This complication is generally referred to as "vitreous loss".

Thus, with the increased interest and desire to perform extracapsular cataract extraction, other complications are encountered with respect to the type and structure of the intraocular lens adapted to be located in the posterior chamber of the human eye.

An article entitled "Posterior Chamber Intraocular Lens Implant Centration: In Or Out of 'The Bag'" was presented by Samuel L. Pallin, M.D. and Gerald B. Walman, M.D., both of Sun City, Ariz., at the U.S. Intraocular Lens Symposium, Los Angeles, Calif., in April of 1982 and was reprinted in *American Intra-Ocular Implant Society Journal*, Volume 8, Summer 1982. The article discusses the comparison between 61 posterior chamber lenses implanted using the "in the bag" technique, wherein the basement membranes of the crystalline lens epithelium (the capsule) is the supporting element, and 150 posterior chamber lenses implanted in the ciliary sulcus. The operative results were evaluated to determine the success of centration in each of the two techniques. The article specifically notes the problem of discouraging adhesions of iris tissue to intraocular lenses associated with posterior chamber lenses implanted in the ciliary sulcus.

One known intraocular lens adapted to be positioned in the posterior chamber of the eye is described in U.S. Pat. No. 4,159,546. This intraocular lens is generally referred to as a Shearing-type lens and comprises a plastic lens body having a plurality of flexible and memory retaining non-biodegradable strands, each strand having one end thereof secured to the lens body and with the other lens thereof unsecured and adapted to function as a spring-like strand which may be biased and urged against the ciliary body of the eye to both support, center and fix the lens in position.

Another intraocular lens adapted to be located in the posterior chamber of the eye is described in U.S. Pat. No. 4,244,060. The intraocular lens described in U.S. Pat. No. 4,244,060 includes a lens body and a plurality of lens-centering filaments which extend outwardly in a common plane from spaced rim portions of the lens body. When the filament ends of the intraocular lens are inserted into the cleft of the capsule, the resilience of the filaments function to center the lens behind the pupil. The intraocular lens described in U.S. Pat. No. 4,244,060 includes an annular lip, or ridge, which projects rearwardly from the rear surface of the lens body. The annular lip, or ridge, is adapted to provide a barrier for preventing vitreous fluid from coming forward into the interior chamber in the event a discission surgery has been performed on the posterior capsule, which results in an opening therein and through which vitreous fluid can migrate.

Iolab Corporation offers for sale a Model 103 posterior chamber lens having a disc-shaped lens and a pair of curved loop legs mounted on the rims thereof with one of the models, Model 103L, having the loops extending at an angle commencing near the edge of the rim and in a direction towards the anterior surface of the lens.

SUMMARY OF THE PRESENT INVENTION

The intraocular lens of the present invention is a new, improved and unique device which is adapted to be implanted in the posterior chamber of the eye after intracapsular or extracapsular cataract extraction. In the preferred embodiment of the present invention, the intraocular lens comprises a lens body having a geometrical dimension which is adapted to pass through the iris of an eye. The intraocular lens further includes a pair of pliable loops, each having a generally planar mounting end located at one end thereof and the other end thereof which terminates in a supporting end which extends at a selected angle from the mounting end. The mounting end of the pliable loops are formed into a generally arcuate shape which has an outer dimension which is less than the geometrical dimension of the lens body. The mounting end terminates in a protuberant member having a predetermined length which extends substantially normal from the plane of the mounting end in a direction of the angle defined by the supporting end. The supporting end of each of the pliable loops has the distal end thereof formed into an arcuate-shaped loop which is located in a plane which extends at the selected angle to the mounting end. Each of the pliable loops has a proturberant member affixed posteriorly to the lens body at a selected location. The arcuate-shaped mounting ends of each loop cooperate to define a posterior capsule framework or barrier which is adapted to be positioned contiguous to the posterior capsule of an eye and define a space between the lens and the posterior capsule.

There are several known disadvantages of the prior art intraocular lens which are overcome by the teachings of the present invention. One disadvantage of the known prior art lens is that the posterior capsule may adhere to, opacify or otherwise form membrane with the posterior portion of the lens body or of the peripheral ridge, or rim, thereof which is contiguous to the posterior capsule. In order to open any membranes which may form post-operatively between the posterior capsule and the lens body, it is known in the art to utilize a YAG laser to separate the cloudy membranes from the posterior capsule. The use of a YAG laser causes a momentary eruption causing severance of the membranes, but the resulting shock wave may result in the pitting or eroding of the lens surface as described in an article entitled "Laser Damages Compared In Glass and PMMA Lenses," which appeared in the June 15, 1983, issue of *IOL and Ocular Surgery News* at pages 4 and 5. This is highly undesirable.

Also, in certain instances, it is desirable to perform a standard capsulotomy surgery utilizing a needle. The known prior art intraocular lenses make it extremely difficult for the surgeon to perform such standard capsulotomy surgery using a needle due to the intimate contact and lack of spacing between the posterior portion of the lens body and the posterior capsule which becomes affixed thereto.

Thus, one advantage of the present invention is that the pliable loops are affixed on a predetermined pattern to the posterior surface of the lens to define a posterior capsule barrier which establishes and maintains a distance between the posterior capsule and the posterior surface of an intraocular lens.

Another advantage of the present invention is that the predetermined distance between the posterior surface of the intraocular lens and the posterior capsule permits safer use of a YAG laser to open any membranes which may form post-operatively on the posterior capsule.

A still further advantage of the present invention is that the predetermined distance or gap formed between the posterior capsule and the posterior surface of the intraocular lens permits a surgeon to more easily perform a standard capsulotomy surgery with a needle.

A still further advantage of the present invention is that the posterior capsule barrier defined by the pliable loops, which in the preferred embodiment may be substantially 360 degrees, creates a firm or raised lip which reduces Elschnig pearl formation.

A still further advantage of the present invention is that the posterior capsule barrier, when positioned contiguous to the posterior capsule, can actually stretch the posterior capsule, thereby permitting a surgeon to more easily utilize a YAG laser to open any membranes or to otherwise perform a standard capsulotomy surgery with as needle.

A still further advantage of the present invention is that the intraocular lens of the present invention can be implanted by a surgical technique and method wherein the lens is first passed through the anterior chamber of the eye where one of the two flexible loops is then positioned through the iris into the posterior chamber until the inferior iris intercepts or contacts the protuberant member, whereupon the second of the pliable loops can be moved from the anterior chamber to the posterior chamber and whereupon the lens body can then be transported through the iris, placing the posterior capsule barrier into engagement with the posterior capsule and positioning the lens body in the posterior chamber of the lens and wherein the supporting ends of the pliable loops are located in the ciliary sulcus.

In the preferred embodiment of the present invention, the loops act as a guide for the surgeon to prevent advancement of the lens to the extreme inferior pole. If the lens otherwise were permitted to advance to the extreme inferior pole, undue pressure may be placed on the inferior zonular structures, causing tearing or stripping thereof. If the zonular structures are torn, the intraocular lens may decenter inferiorly.

Another advantage of the present invention is that the lens may be implanted in such a manner that the loops act as a guide to keep it in front of the pupil until such time as the surgeon desires to place the lens behind the iris. The loops support the lens in this position to ensure that the lens will not be "dropped" by the surgeon or that the lens will not inadvertently disengage from the instrument during implantation. If the lens is either dropped or becomes disengaged from the instrument during surgery, the lens may be lost through a zonular or capsule tear and fall through the vitreous fluid to the retina.

Another advantage of the present invention is that the lens is located at a position rearward of the pupil and in front of the vitreous fluid. The angled loops of the intraocular lens are placed into the ciliary sulcus resulting in minimum disturbance to the face of the vitreous fluid during insertion in an intracapsular procedure. Further, in the intracapsular procedure, the loops of the intraocular lens can be safely placed into and rest in the ciliary sulcus due to the absence of zonular structure or capsule, avoiding contact of the vitreous fluid by the lens. The barrier or framework of the loops applies pressure against the vitreous fluid to counter any pressure forward of the vitreous fluid.

A yet further advantage of the present invention is that the intraocular lens disclosed herein can be positioned in the posterior chamber of the eye following either intracapsular or extracapsular cataract extraction.

A still further advantage of the present invention is the intraocular lens described herein is simple in design and can be fabricated from known materials and using known manufacturing techniques which are well known in the art.

BRIEF DESCRIPTION OF THE DRAWING

The foregoing and other advantages and features of this invention will become apparent from the following description of the preferred embodiment when considered together with the illustrations and accompanying drawing which includes the following figures;

FIG. 1 is a pictorial representation of a human eye having the intraocular lens of the present invention located in the posterior chamber thereof;

FIG. 2 is a top plan view showing the lens body and preferred location of the pliable loops affixed thereto;

FIG. 3 is a front plan view of the intraocular lens of FIG. 2;

FIG. 4 is a right end plan view of the intraocular lens of FIG. 2;

FIG. 5 is a bottom plan view of the intraocular lens of FIG. 2;

FIG. 6 is a front plan view of one of the pliable loops showing the selected angle of the supporting end relative to the plane defined by the mounting end;

FIG. 7 is a top plan view of the pliable loop illustrated in FIG. 6;

FIGS. 8(a), 8(b), 8(c) and 8(d) illustrate four steps for performing a surgical implantation of the intraocular lens of the present invention in the posterior chamber of a human eye;

FIG. 9 is a pictorial representation of a human eye having an intraocular lens in position wherein the posterior capsule has become affixed to the posterior capsule barrier and is severed therefrom by means of a YAG laser;

FIG. 10 is a pictorial representation of an alternate embodiment of the present invention wherein the intraocular lens has three pliable loops; and FIG. 11 is another embodiment of an intraocular lens of the present invention having two pliable loops wherein the arcuate shape defined by the mounting ends has a geometrical dimension which is greater than the arcuate-shaped dimension of the mounting ends.

DESCRIPTION OF THE PREFERRED EMBODIMENT

In the human eye illustrated in FIG. 1, the intraocular lens 20 is located within the human eye shown generally as 22. The human eye includes a cornea 24. The cornea 24 encloses the anterior chamber 26. The portion of the eye located posterior to the iris 28 is the posterior chamber, which is shown generally as 30. In an extracapsular cataract extraction, the posterior capsule 32 is left intact along with the suspensatory ligaments 34. The area located between the posterior capsule 32 and the iris 28 is the ciliary sulcus 40.

The intraocular lens 20 illustrated in FIG. 1 includes a lens body 50 having an anterior surface 52 which is located toward the interior chamber 26 and a posterior surface 56 which is located towards the posterior chamber 30. The lens body 50 has a geometrical dimension which is adapted to permit the same to be passed through the pupil defined by the iris 28.

The intraocular lens 20 further includes a pair of pliable loops shown generally as 60 and 62 which have a generally planar mounting end and a supporting end. The details of the construction of the intraocular lens 20 are illustrated in detail in FIGS. 2 through 5. As illustrated in FIG. 1, the supporting ends of the pliable loops 70 and 72 are adapted to be located in the ciliary sulcus 40. As illustrated in FIG. 1, the pair of pliable loops 60 and 62 define a posterior capsule framework or barrier which is contiguous to the posterior capsule 32. When mounted, the posterior capsule 32 is slightly stretched over the framework or barrier defined by the mounting end of the pliable loops 60 and 62. Thus, the posterior capsule 32 is maintained at a selected space, generally shown as space 80, from the posterior surface 56 of the lens body 50.

Referring now to FIGS. 2 through 5, the construction of the intraocular lens of the preferred embodiment is shown. The lens body 50 has a geometrical dimension which is adapted to permit the entire lens body 50 to pass through the iris, for example, iris 28 as illustrated in FIG. 1. The intraocular lens 20 includes a pair of pliable loops 60 and 62 which have generally planar mounting ends 84 and 86, respectively, located at one end thereof and an opposite end thereof which terminates in supporting ends 70 and 72, respectively, each of which extends at a selected angle from the mounting ends. The mounting ends 84 and 86 are formed into a generally arcuate shape having an outer dimension which is less than the geometrical dimension of the lens body. Also, each of the mounting ends 84 and 86 terminate in protuberant members 94 and 96, respectively, each of which has a predetermined length and each of which extends substantially normal from the plane of the mounting ends 84 and 86. The protuberant members 84 and 86 extend in a direction of the angle defined by the supporting ends 70 and 72. The supporting ends 70 and 72 have the distal end thereof formed into an arcuate-shaped loop which is located in a plane which extends at a selected angle to the mounting ends 84 and 86. The pair of pliable loops 60 and 62 are affixed with the protuberant members 94 and 96 affixed posteriorly to the lens body on the posterior surface 56 and at selected locations such that the arcuate-shaped mounting ends 84 and 86 define a posterior capsule barrier or framework which is adapted to be positioned contiguous to a posterior capsule of an eye. The posterior capsule barrier defined by the mounting ends 84 and 86 also defines a space between the posterior surface 56 of the lens body 50 and the posterior capsule 32 as shown in FIG. 1.

FIGS. 6 and 7 are views showing pliable loop 60. The pliable loop 60 has a mounting end 84 which is formed into a generally arcuate shape and which terminates in the protuberant member 94. The opposite end of the pliable loop 70 terminates in an arcuate-shaped loop which is located in a plane which extends at a selected angle relative to the plane defined by the mounting end. In the preferred embodiment, the supporting end commences its angular disposition relative to the plane of the mounting end at a point 100, which point 100 is generally located at approximately the outer peripheral edge of the lens body. The selected acute angle, illustrated as angle $\phi$ in FIG. 6, may vary from approximately 2 degrees to about 15 degrees, with a preferred range of angles of approximately 5 degrees to 8 degrees and with the preferred angle being approximately 5 degrees.

Referring again to FIGS. 2 through 5, inclusive, the lens body 50 further includes position holes shown generally as 82 to permit the surgeon to utilize surgical tools to cause the implantation of the intraocular lens into the eye. This permits a surgeon to first insert one pliable loop into the posterior chamber and into the ciliary sulcus 40; then the other end of the pliable loop is inserted into the posterior chamber and into the ciliary sulcus 40. If desired, the lens may be left in this position. If the surgeon desires to have the lens located in the posterior chamber, then the entire lens body may be transported from the anterior chamber into the posterior chamber while urging the posterior capsule barrier, defined by the loops, contiguous to the posterior capsule 32.

The loops of the present invention are designed such that they extend anteriorly from the lens. This anterior angle works uniquely in conjunction with the loops, which extend at substantially right angles from the location where the same are heat-welded to the lens body. As the inferior loop is placed behind the iris, its angulation helps to slide the loop along the back side of the iris or in the proximity of the iris, keeping the loop from accidentally being placed within the capsular bag. Thus, the ends of the loops, which are not visible to the surgeon during the implantation, must be moved or positioned behind the inferior iris toward the ciliary sulcus. During implantation, the lens is not pushed behind the pupil during initial insertions; and the stops or pegs of the loops, at the point where the same extend at a substantial right angle from the lens, are used by the surgeon as guides as well as a means to prevent damage to the eye or the loss of a lens during insertion.

Once the lens is in position, the anterior angulation of the loops acts to keep the lens from becoming trapped in the pupil opening while the remaining portion thereof acts to keep the lens from being placed too far posteriorly, such that forming an opening in the posterior capsule would be difficult, even using a YAG laser or other surgical instruments. The intraocular lens design maintains a dynamic balance between the anterior-posterior axis.

The method for performing the implantation of the intraocular lens of the present invention is illustrated in FIGS. 8(a) through 8(d), inclusive. The procedure illustrated in FIG. 8(a) through 8(d) is subsequent to the extracapsular cataract extraction surgery. The cornea 24 has a small slit formed therein, as illustrated by slit 102, such that the intraocular lens 20 can be inserted into the anterior chamber 26 of the eye. Thereupon, one of the pliable loops, such as pliable loop 60, is directed posterior to the iris 28 until the inferior iris 104 engages the protuberant member 96 and such that the supporting end 70 is located in the ciliary sulcus 40. This is illustrated in FIG. 8(a).

Thereupon, and as illustrated in FIG. 8(b), the surgeon then deflects the other supporting end 62 through the iris 28 as illustrated in FIG. 8(b).

When the supporting end 72 of the pliable support 62 is positioned in the ciliary sulcus 40, the lens body 50 is located completely within the anterior chamber 26 and forward of the iris 28. When the intraocular lens has been moved into the position illustrated in FIG. 8(c), the surgeon then, if desired, with the use of surgical tools, urges the lens body 50 through the pupil 28 into the posterior chamber 30 as shown in FIG. 8(d). The flexible loops 60 and 62 define a posterior capsule barrier, shown generally as 106, which is placed contiguous to or in contact with the posterior capsule 32. When the implantation is completed, a distance 80 is maintained between the posterior capsule 32 and the posterior surface 56 of lens body 50.

FIG. 9 illustrates a post-operative treatment for removing the posterior membrane 32 which has opacified or, in some cases, become affixed to the posterior barrier 106. As illustrated in FIG. 9, a device known as a YAG laser 110 directs a laser beam 112 through the cornea 24, through the lens body 50 and focuses the same just rearward, or posterior, the posterior capsule framework of barrier 106. The YAG laser 110 causes the laser beam 112 to produce a slight eruption which severs the membrane 32 at the locations where the same have opacified to the posterior capsule barrier 106. Of importance is that the posterior capsule 32 does not come into an engagement with the posterior surface 56 of the lens 50.

FIG. 10 illustrates another embodiment having three barrier loops 120, 122 and 124 which are affixed at predetermined locations to the lens body 126. The intraocular lens illustrated in FIG. 10 is a bottom view and shows that the mounting portions thereof generally define a posterior capsule barrier shown generally as 130.

FIG. 11 shows another embodiment of an intraocular lens having a lens body 140 which has two pliable loops 142 and 144. The pliable loops 142 and 144 differ from the loops illustrated in FIG. 7 by the fact that the supporting end 150 of resilient support 142 is greater than the mounting end 152 of support 142. Likewise, resilient support 144 has its support in 160, which has a greater geometrical dimension that the geometrical dimension of the arcuate-shaped mounting end 162. In the preferred embodiment illustrated in FIG. 1, the cross-sectional area of the lens illustrates that the lens is plano-convex in shape. However, the lens may be formed of any desired shape or geometrical dimension. Further, the lens may be fabricated from glass or a plastic material. The lens body may be formed from a clear plastic material such as polymethylmethacrylate, which is well known in the art. The resilient support members may likewise be formed of the same material or may be formed from polypropylene. The dimensions of the lens body may be in the order of 6.0 millimeters. The total geometrical dimension from the ends of each of the posterior loops from supporting end to supporting end may be in the order of 13.5 millimeters. The distance traversed by the supporting end relative to the plane of the mounting end may be in the order of 1.0 millimeters but may be as high as 5.0 millimeters depending on the selected angle. The distance between the mounting ends affixed to the posterior surface of the lens body and which define the posterior capsule barrier may have a dimension in the order of 4.0 millimeters.

The pliable plastic loops may be either bonded to the lens body or holes may be drilled in appropriate locations of the lens body approximately 1.0 millimeters to 1.55 millimeters from the edge of the lens and the loops heat-welded in the holes. The pattern defined by the ends of the resilient loops may be either a J-loop or C-loop pattern, as illustrated in FIGS. 2, 10 and 11.

In the preferred embodiment, the lens body consists of a 6-millimeter optical disc material made of plastic as described herein and having a plano-convex design wherein the convex side of the lens is designed to be placed anteriorly relative to the eye.

What is claimed is:

1. An intraocular lens comprising
   a lens body having a geometrical dimension which is adapted to pass through the iris of an eye; and
   a pair of pliable loops each having a generally planar mounting end located at one end thereof and an opposite end thereof which at a predetermined point terminates in a supporting end which commences an angular disposition having a selected angle relative to the plane of said mounting end, said mounting end being formed into a generally arcuate shape having an outer dimension which is less than said geometrical dimension and which terminates in a protruberant member having a predetermined length and which extends substantially normal from the plane of the mounting end and in a direction of the angle defined by said supporting end, said supporting end having the distal end thereof formed into an arcuate-shaped loop located in a plane which extends commencing at said predetermined point at said selected angle to the plane of said mounting end;

said pair of pliable loops having said protruberant members posteriorly to said lens body at selected locations with said predetermined points located at approximately the outer peripheral edge of the lens body wherein said arcuate-shaped mounting ends define a generally planar posterior capsule barrier which is adapted to be positioned contiguous to a posterior capsule of an eye while being capable of defining a space between the lens and said posterior capsule.

2. The intraocular lens of claim 1 wherein said lens body is generally in the shape of a disc.

3. The intraocular lens of claim 2 wherein said protrudent members of said pliable ends are located in holes formed into the posterior surface of said lens body and wherein the holes are located approximately 180 degrees relative to each other.

4. The intraocular lens of claim 2 wherein the cross-sectional area defined by said lens is plano-convex in shape.

5. The intraocular lens of claim 1 wherein said selected actute angle is an angle between about 3 degress and about 15 degrees.

6. The intraocular lens of claim 5 wherein said selected angle is between about 5 degrees to about 8 degrees.

7. The intraocular lens of claim 6 wherein said selected angle is about 5 degrees.

8. The intraocular lens of claim 1 wherein the geometrical dimensions of the mounting end is greater than the geometrical dimension of the supporting end.

9. The intraocular lens of claim 1 wherein the geometrical dimension of the mounting end and the supporting end are substantially the same.

10. The intraocular lens of claim 1 when the geometrical dimension of the supporting end is greater than the geometrical dimension of the mounting end.

11. The intraocular lens of claim 1 wherein said lens material is formed of a clear plastic material.

12. The intraocular lens of claim 11 wherein said plastic material is polymethylmethacrylate.

13. The intracular lens of claim 12 wherein said pliable loops are formed of polypropylene.

14. An intraocular lens adapted for implantation in the posterior chamber of an eye after extracapsular cataract extraction or intracapsular cataract extraction comprising
a lens body;
a plurality of pliable loops each having a mounting end which terminates in a protruberant member which is affixed to and extends a predetermined distance from the lens body and which at a predetermined point terminates at an opposite end thereof in a supporting end which commences an angular disposition having a substantially acute angle relative to the plane of said mounting end, said supporting end commencing its angular disposition relative to the mounting end at a point which is located substantially circumferential of the lens body, said mounting ends of said plurality of pliable loops having the protruberant members affixed posteriorly to the lens body at selected locations with said predetermined points located at approximately the outer peripheral edge of the lens body wherein each of the mounting ends are positioned relative to each other to define a generally planar posterior capsule barrier which is adapted to be positioned contiguous to and to slightly stretch the posterior capsule of an eye while defining a space between the lens body and the posterior capsule 15. The intraocular lens of claim 14 wherein said plurality of pliable loops are two.

16. The intraocular lens of claim 14 wherein said plurality of pliable loops are three.

17. In a cataract surgery following extracapsular cataract extraction, a method of implanting an intraocular lens having a lens body and a plurality of pliable loops each having a mounting end with a protruberant member located at one end thereof and an opposite end thereof which at a predetermined point terminates in supporting ends which commences an angular disposition having a selected acute angle relative to the plane of the mounting ends with the predetermined points thereof located at approximately the outer peripheral edge of the lens body and wherein the mounting ends thereof generally define a generally planar posterior capsule barrier which is adapted to be positioned contiguous the posterior capsule comprising the steps of
inserting said intraocular lens through the pupil with one of the plurality of pliable loops being directed past the iris into the ciliary sulcus until the protruberant member engages the inferior iris;
urging the other pliable loop through the iris and into the ciliary sulcus while maintaining the lens body in the anterior chamber of the eye; and
urging the lens body from the anterior chamber past the iris into the posterior chamber and urging the generally planar posterior capsule barrier defined by the mounting ends of the pliable loops into engagement with the posterior capsule and to slightly stretch said posterior capsule across said generally planar posterior capsule barrier enabling the supporting ends of said intraocular lens to remain in the ciliary sulcus and having the supporting ends extend at a selected angle commencing at the predetermined point from the posterior capsule so as to maintain a space between the posterior surface of the lens body, the posterior capsule and the angularly disposed supporting ends.

* * * * *